United States Patent [19]

Ducroo

[11] Patent Number: 4,746,517

[45] Date of Patent: May 24, 1988

[54] PRODUCTION OF BEER

[75] Inventor: Paul Ducroo, Phalempin, France

[73] Assignee: Gist-Brocades S.A., Prouvy, France

[21] Appl. No.: 936,806

[22] Filed: Dec. 2, 1986

[30] Foreign Application Priority Data

Dec. 3, 1985 [EP] European Pat. Off. ........ 85202017.1

[51] Int. Cl.$^4$ .......................... C12C 5/02; C12C 9/00; C12R 1/645
[52] U.S. Cl. ........................................ 426/12; 426/16; 426/29; 426/592; 426/62; 435/911
[58] Field of Search ........................ 426/11, 12, 15, 16, 426/28, 29, 52, 61–64, 590, 592, 600, 330.4; 435/93, 94, 99, 945, 911, 223, 200, 201

[56] References Cited

U.S. PATENT DOCUMENTS

| | | | |
|---|---|---|---|
| 2,011,096 | 8/1935 | Wallerstein | 426/12 |
| 3,366,483 | 1/1968 | Stone | 426/12 |
| 4,110,163 | 8/1978 | Hjortshoj et al. | 426/29 |
| 4,439,455 | 3/1984 | Villettaz | 426/12 |

FOREIGN PATENT DOCUMENTS 2150933 7/1985 United Kingdom.

OTHER PUBLICATIONS

E. B. C. Martin—Beer Stabilization—The Brewers Digest 3/72 vol. 47, pp. 72 to 76.
Jean Comtat—Xylanases from a Basidiomycete—pp. 215 to 231.

*Primary Examiner*—Raymond N. Jones
*Assistant Examiner*—Marianne M. Cintins
*Attorney, Agent, or Firm*—Bierman and Muserlian

[57] ABSTRACT

A process for improving the filterability of wort or beer comprising treating said wort or beer with an enzymatic product produced by *Disporotrichum dimorphosporm* exhibiting xylanase activity in an amount effective to improve the filterability.

4 Claims, 6 Drawing Sheets

Fig.1

Figure 4:
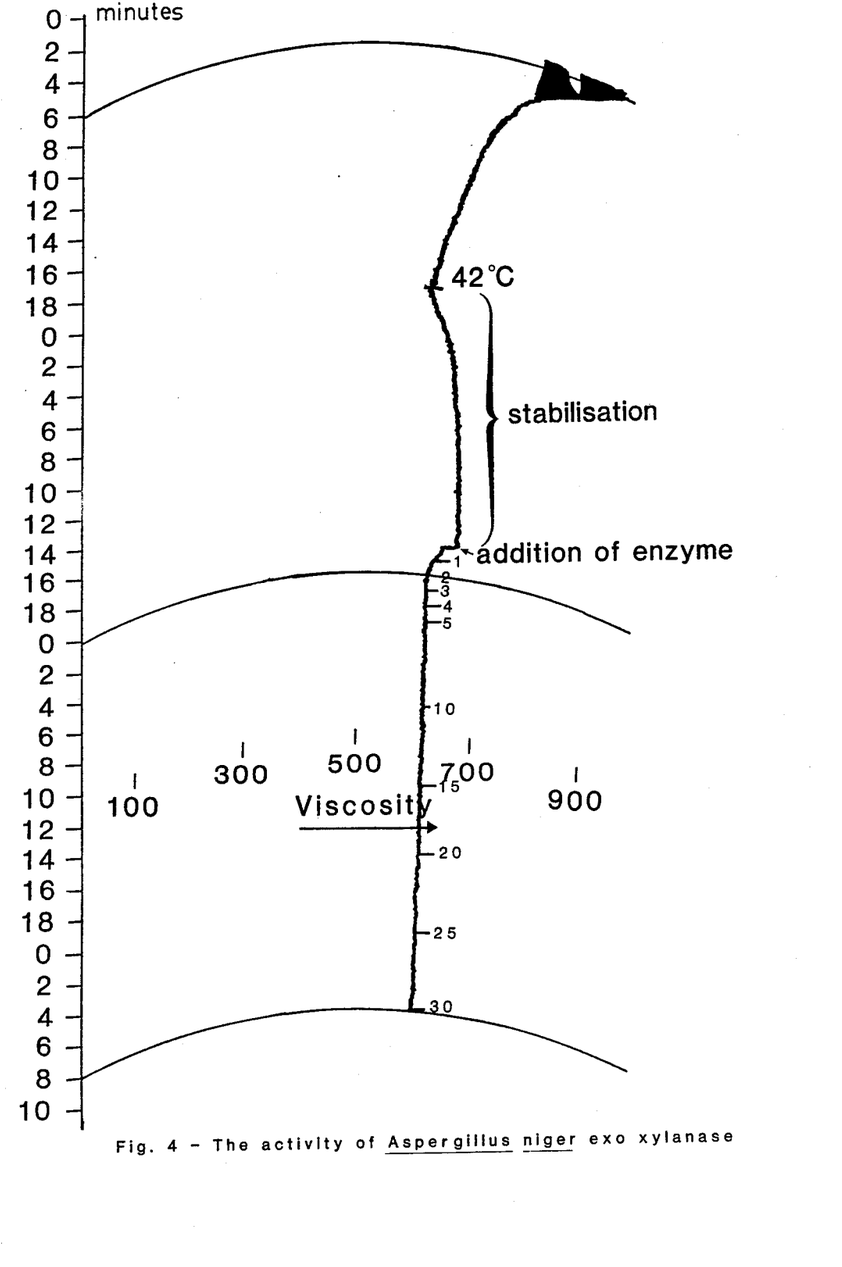

Fig. 4 — The activity of Aspergillus niger exo xylanase

Figure 5:
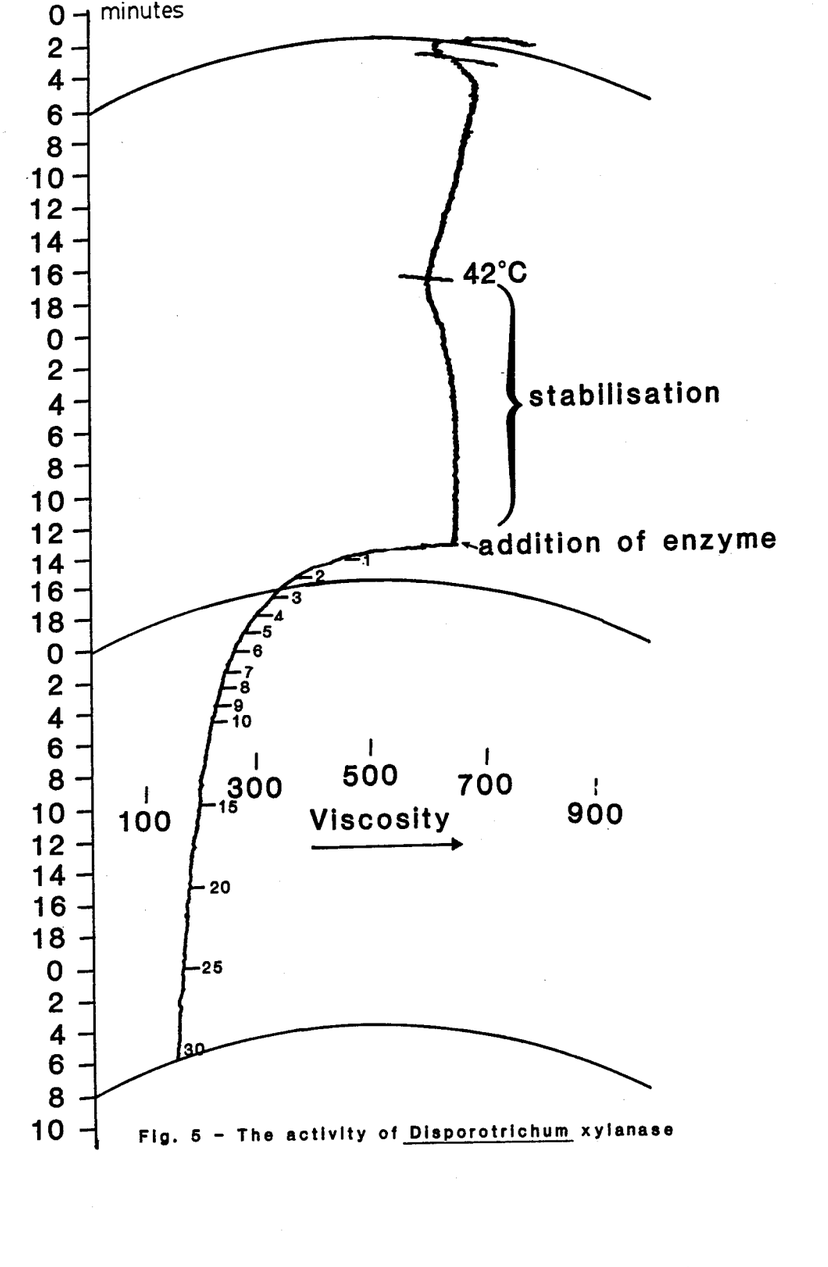

Fig. 5 – The activity of <u>Disporotrichum</u> xylanase

Figure 6:
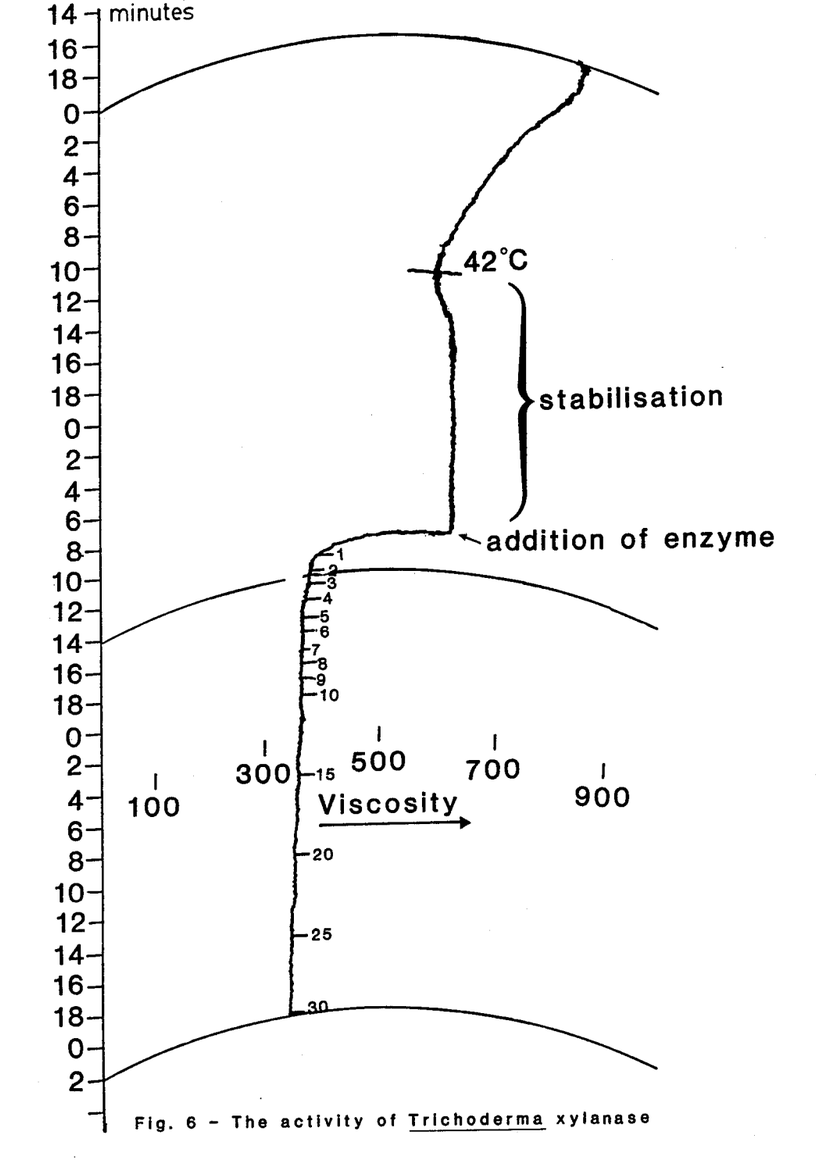

Fig. 6 – The activity of Trichoderma xylanase

PRODUCTION OF BEER

The invention relates to improvements in and relating to the production of beer, especially, but not exclusively, bottom-fermented beer. More specifically, it relates to a process for increasing the filterability and thus the yield of the wort or beer and for improving the colloidal stability of beer during the maturation process.

Beers are manufactured from grains which are naturally low in fermentable sugars. The starch of the grains must therefore be saccharified (i.e. hydrolysed to the fermentable sugars, maltose and glucose) before fermentation by yeasts. Barley contains little or no amylase, but upon germination large amounts of amylase are formed. Hence, barley is dampened, allowed to germinate, and then dried and stored for subsequent use. Such dried, germinated barley, is called malt. In Europe, barley malt is traditionally used for the production of beer. To saccharify the starch in barley, the starch-hydrolysing enzymes (amylases) of the barley malt itself are used.

Hence, the first step in beer making is malting. The malt is then ground and suspended in water to allow further hydrolysis of the starch and extraction of fermentable sugars. Several starch degrading enzymes, for example alpha-amylase, beta-amylase, amyloglucosidase and debranching enzymes like pullulanase, can be added to the suspension to improve the fermentability of the extract. After saccharification has reached the desired stage, the mixture is boiled to stop further enzymatic changes and then filtered. Hop extract, which imparts the characteristic bitter flavour of beer and which also acts as a preservative against the growth of bacteria, is added to the filtrate. The hopped filtered extract of fermentable sugars, which is called wort, is then ready for fermentation.

In beer fermentations, the wort is always heavily inoculated with special strains of yeast derived from a previous fermentation. The fermentation proceeds at low temperatures for 5 to 10 days. Most of the yeast strains used in making beer belong to the species *Saccharomyces carlsbergensis* and *Saccharomyces cerevisiae*. During the fermentation the fermentable sugars are converted into ethanol and characteristic flavour compounds are produced.

After the fermentation most of the yeast is removed and the green beer is stored in lager tanks for a variable period of time to mature.

The use of low quality malt or the replacement of part of the malt by barley or wheat in the brewhouse makes it necessary to add beta-glucanase and sometimes alpha-amylase and protease to the wort to reduce its viscosity and to increase brewhouse yield. Beta-glucanase may also be added to beer during lagering or cold storage to improve filter throughput, beer brilliance and colloidal stability with corresponding savings in filter aid requirements. Beta-glucans are made of very long chains of 1,4-beta-D-glucopyranose (70% of linkages) and 1,3-beta-D-glucopyranose (30% of linkages). Their molecular weight is about 200,000. Solutions of beta-glucans are highly viscous, and beta-glucans often therefore give filtration problems in brewing. At present, beta-glucanases derived from *Bacillus subtilis*, *Aspergillus niger* and *Penicillium emersonii* are commercially available to solve problems of filterability caused by beta-glucans on an industrial scale.

Figure 1:
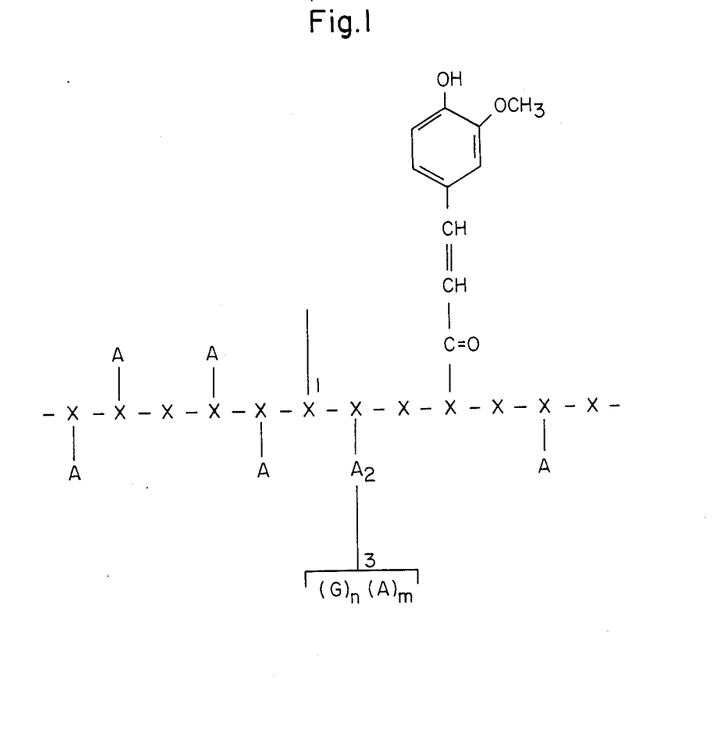

Besides beta-glucans, some pentosans occur in barley and wheat gums. Pentosans are less well known than beta-glucans and their structure is more complicated with long chains of 1,4-beta-D-xylopyranose and single 1,2- or 1,3-alpha-L-arabinofuranose side groups (in the ratio of 1 arabinose to 2 xylose units); see accompanying FIG. 1, proposed by H. Neukom, L. Providoli, H. Gremli and P. A. Jui, Cereal Chem., 44, 238 (1967).

The properties of pentosans vary with the presence or absence of peptides, ferulic acid and arabinogalactan. About ⅔ of total pentosans are insoluble because of their high molecular weight and some interlinkages with proteins and other constituents. They have a very high water retention power and give very bulky spent filtration cakes. When arabinofuranose side groups of soluble pentosans are hydrolysed, an association and precipitation of non-substituted xylans is observed.

The average pentosan content of various cereals is as follows (see "Handbuch der Lebensmittelchemie", Vol. 5, p. 32, 1967, Springer Verlag):

| Cereal grain       | Pentosans (% dry weight) |
|--------------------|--------------------------|
| Barley (incl. husks) | 10.3                   |
| Wheat              | 7.4                      |
| Rye                | 10.6                     |
| Oats (incl. husks) | 7.5                      |
| Corn               | 6.2                      |
| Rice               | 2.0                      |
| Millet             | 2.0                      |

British Specification No. 1,421,127 describes a process for the preparation of an enzyme solution with beta-1,4/beta-1,3-glucanase activity from *Penicillium emersonii*, recommended for use in brewing to improve the filterability of the wort.

Coote and Kirsop (J. Inst. Brew., 82, 34 (1976) state that certain hazes appearing in high gravity beer contain 88% of pentosans.

British Specification No. 2,150,933 describes a pentosanase obtained by fermentation of *Talaromyces* (i.e. *Penicillium*) *emersonii*. This enzyme is stated to be capable of catalysing the degradation of xylan and to be useful for improving the production and extraction of fermentable sugars in brewing and for the prevention or treatment of certain types of haze.

We have now surprisingly found that an endoxylanase produced by the fungus Disporotrichum has especially valuable properties as an agent for improving the yield and filterability of wort or beer.

Disporotrichum, and in particular *Disporotrichum dimorphosporum*, has been described by J. A. Stalpers, Studies in Mycology, 24, 1 (1984).

The present invention accordingly provides a process for producing wort or beer of improved filterability and/or lower viscosity which comprises subjecting the said wort or beer to the action of Disporotrichum xylanase.

Preferably, a xylanase preparation is used derived from *Disporotrichum dimorphosporum*. Very satisfactory results are obtained when using a xylanase preparation derived from *Disporotrichum dimorphosporum* strain ATCC 24562, available from the American Type Culture Collection, which is identical with strain CBS 484.76, available from the Centraal Bureau voor Schimmelcultures, Baarn, Netherlands. These strains are preferred for the purpose of this invention.

Other xylanase preparations which may be used according to the present invention are those having substantially the same characteristics as the xylanase preparation which is obtainable from *Disporotrichum dimorphosporum* strain ATCC 24562 (or CBS 484.76). This includes preparations obtained from a transformed host microorganism containing the gene coding for the xylanase produced by said Disporotrichum strain ATCC 24562 (or CBS 484.76).

From a technical point of view, an endo-type enzyme is generally preferable because it hydrolyses high molecular weight polysaccharides very rapidly. An exo-type enzyme requires more time and more enzymatic concentration in order to reach the same technological result.

Generally, activities of pentosanases or xylanases are measured on commercial substrates which are obtained from larchwood xylan or oat huskes xylan and which have a structure completely different from cereal xylans substrate. After enzymatic action under precise pH and temperature conditions, enzymatic activities are evaluated by determination of reducing sugars. With this method, it is not possible to distinguish whether the enzyme is an endo or an exo type or a blend thereof. Moreover, the present commercial substrates are also more or less denaturated by purification treatments.

According to another aspect of the invention a method is provided for measuring endoxylanase activity. With the aid of this new and original method we were capable of selecting the most efficient enzymes for the purpose of this invention.

The method for the determination of endo-xylanase activity is based on the measurement of the viscosimetric activity of the enzyme on a natural rye pentosan substrate, as will be outlined in more detail in the following Examples. In this method the modification of natural substrate by heat treatment or drastic alkaline or acid pretreatment has been avoided in order to keep some selectivity on enzymatic determinations.

Using said new method is has been found in comparative tests that *Disporotrichum dimorphosporum* pentosanase presents the most interesting properties for hydrolysis of pentosans from cereal origin.

A concentrate of Disporotrichum xylanase suitable for use in the present invention may be obtained in the following manner. The fermentation is carried out in a sterile tank and medium in known manner. The culture medium contains cellulose, pectin, yeast extract and appropriate salts. It is inoculated with a pure culture of *Disporotrichum dimorphosporum*. the fermentation is effected at a constant temperature between 20° C. and 37° C., preferably about 32° C., and the pH is maintained within the range of 3.0 and 6.0, preferably 4.0 to 4.5. The fermentation can be batchwise or continuous. The xylanase activity is followed during the process. It is not necessary to induce the production of the enzyme by addition of xylan-containing materials (e.g. corn cobs or flours), and the addition of such products mainly promotes the formation of an exo-xylanase, which is less useful for the invention. When the required enzymatic activity has been reached the mash is harvested, filtered and concentrated by vacuum concentration or ultrafiltration. The concentrate can be sold as a liquid preparation or spray dried in a powder form. The endoxylanase hydrolyses the 1,4-beta-xylose linkages within the pentosan chains.

Figure 2:
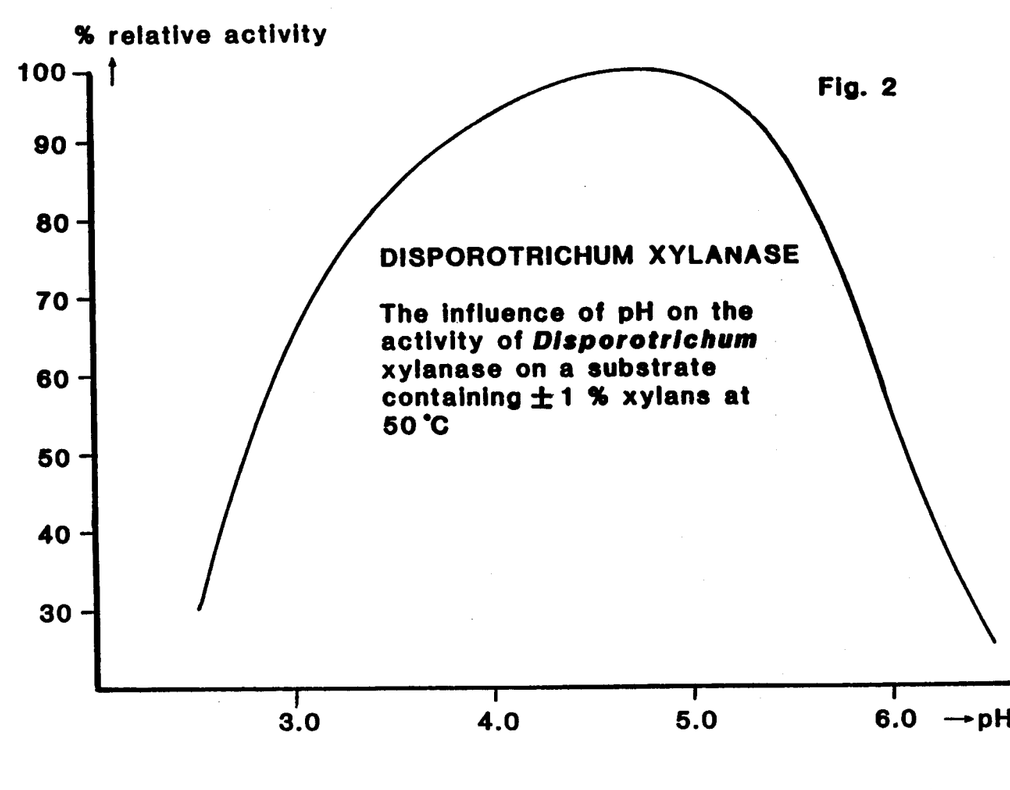
Figure 3:
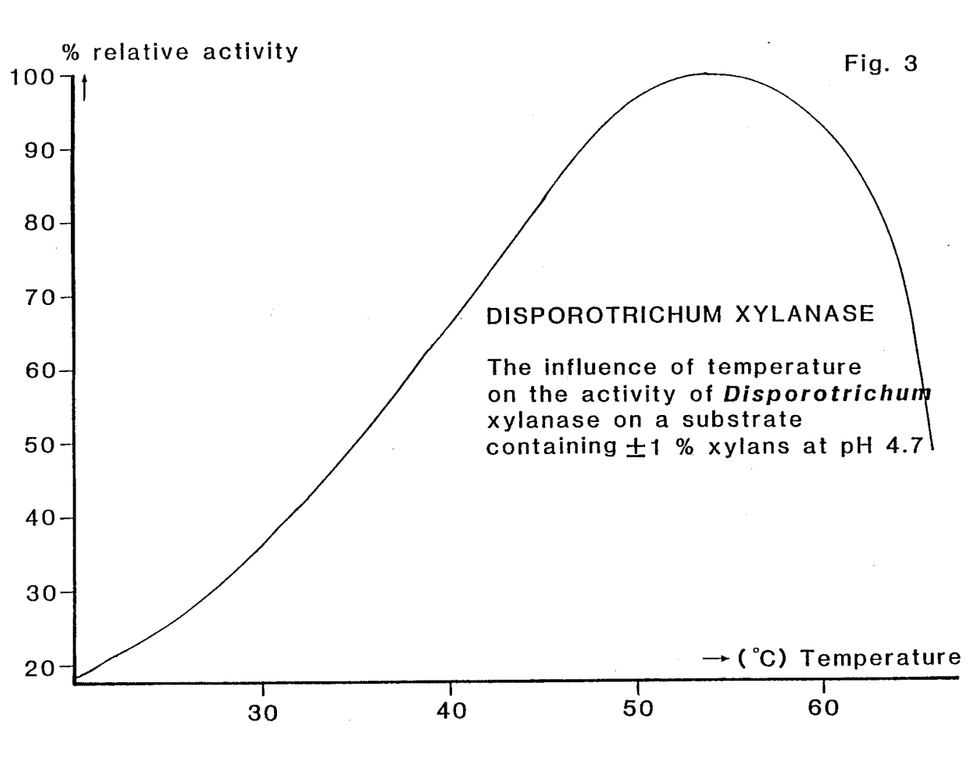

The effect of the non-purified enzymatic product on a substrate containing ±1% xylans has been studied viscosimetrically (see FIGS. 2 and 3). The optimum pH is 4.7 but between pH 3.0 and 6.0 the relative activity is more than 50%. The optimum temperature is 55° C. but more than 50% relative activity remains at 65° C. Purification of this Disporotrichum xylanase was studied by Comtat et al. (J. Comtat, K. Ruel, J. -P. Joseleau and F. Barnoud, Symposium on Enzymatic Hydrolysis of Cellulose, S.I.T.R.A., Helsinki, Finland, 351 (1975); J. Comtat and J. -P. Joseleau, Carbohydr. Res., 95, 101 (1981)).

The Disporotrichum xylanase can be used with other additives in the brewing process, e.g. the usual chillproofing agents, for example, papain, polyvinylpyrrolidone and tannic acid, and various other enzymes described inter alia in U.S. Pat. Nos. 3,061,439, 3,095,358, 3,749,582 and 3,770,454 and in Canadian Pat. No. 743,524. It is surprising that the xylanase is effective in brewing because the beta-glucan-pentosan ratio in barley gum is 4:1, but this may be due to the higher water retention capacity of the pentosans.

Papain, a vegetable protease, is widely used to improve the colloidal stability of beer by hydrolysis of proteins. The addition of Disporotrichum xylanase to papain in the lagering tank produces a complementary effect on colloidal stability and improves the filterability of the beer. The addition of the xylanase is particularly preferred when wheat or barley are used in the mash or when the malt is of poor quality.

Disporotrichum xylanase appears to be better suited for use in brewing than other xylanases. For example, when Trichoderma and Disporotrichum xylanases are compared, there is a large difference of their efficiency in viscosity tests in which Disporotrichum xylanase is superior.

The xylanase (pentosanase) disclosed in British Specification No. 2,150,933 is stated to have optimum activity against oat hull xylan at 87±2° C. and to retain 50% of its initial activity after heating at 95° C. for six minutes at pH 5.0. This is an undesirably high degree of thermal stability for an enzyme to be used in brewing at the fermentation step since it means that the enzyme will not be appreciably denatured during the normal beer pasteurization process. The Disporotrichum xylanase is however almost entirely denatured under these conditions.

Disporotrichum xylanase may be added to beta-glucanase enzyme solutions to improve their properties. The addition of Disporotrichum xylanase provides an improved effect on wort and beer viscosity, extraction and filterability. By reducing the wort viscosity and the water retention capacity of spent grain, Disporotrichum xylanase makes it possible to increase the brewhouse capacity by producing higher density brews. Especially when wheat or barley (with a large pentosan content) is used in the brewhouse, Disporotrichum xylanase can be used to solve problems relating to the filterability of wort and beer.

The xylanase derived from *Penicillium emersonii* (British Specification No. 2,150,933) shows the same type of viscosity degrading activity as that demonstrated by Disporotrichum xylanase, but the level of activity of *P. emersonii* xylanase is much lower (usually from about 10 to about 40% of the activity of Disporotrichum xylanase). However, because of this lower activity, the addition of Disporotrichum xylanase to the *P. emersonii* enzyme solution improves the efficiency of the product. *P. emersonii* xylanase is thermostable (optimum temperatures 85°–87° C.) but beta-glucans and pentosans are freed in the wort at only about 65° C. when starch gelatinizes. At this temperature, Disporotrichum xylanase has kept over 50% residual activity which is sufficient to hydrolyze the rest of pentosans freed at this temperature. Moreover, a temperature of 85° C. is never used in the brewing process, which never passes above 76° C.

The action of Disporotrichum xylanase in the brewhouse has an effect on beer filterability, but when Disporotrichum xylanase has not been used in brewhouse, it is still possible to add it in the lagering tank with or without beta-glucanase to improve the filterability of beer and obtain the consequent savings (e.g. in labor, filtration plates, losses etc.). Of course, Disporotrichum xylanase can be used both in the brewhouse and in lagering tank. Beer so made needs less pressure during the filtration cycle, is more brilliant coming out of the filter, and has improved colloidal stability. It appears difficult to use *Penicillium emersonii* xylanase in the lagering tank because its activity is not inactivated in the normal pasteurization of the beer.

The colloidal stability of beer treated with Disporotrichum xylanase has been examined with the alcohol cooling test. The addition of beta-glucanase derived from *Bacillus subtilis* with an excess amount of papain (a dose which exceeds the amount which gives the maximum effect on stability) to the lagering tank does not change the colloidal stability of beer compared to the addition of papain itself. However, if Disporotrichum xylanase is added with the excess dose of papain the minumum haze value of the beer is still further decreased.

The advantageous properties of Disporotrichum xylanase are also useful in the manufacture of ale type beer made by top fermentation.

The following Examples are given by way of illustration. In the Examples the procedure for endo-xylanase activity determination, which was used unless otherwise stated, was conducted as follows.

PROCEDURE FOR ENDO-XYLANASE ACTIVITY DETERMINATION

The analytical method is derived from the method exemplified in Example I.

A. Principle

The method is based on the measurement of the viscosimetric activity of the enzyme on a natural rye pentosan substrate.

The variation of the inverse of the specific viscosity (1/ns) versus the time of the action of the enzyme makes it possible to determine an apparent kinetics constant which is proportional to the specific activity of the enzymatic preparation.

B. Apparatus

A water-bath regulated at 42° C.±0.1° C.
A capillary viscosimeter with a flow constant close to 0.03
Ubbelhode viscosimeter No. IC or Prolabo viscosimeter type UF
two stop-watches
a filter
a pH meter
a centrifuge

C. Reagents

C1. Pentosan substrate

This substrate is extracted from rye flour type 170 (according to French legislation, grey flour quality). This rye flour is selected on the basis of:
high viscous pentosans content (according to Drews method, see Example I)
low natural pentosanase activity A slurry of 300 g rye flour and 1 liter distilled water at 42° C. is prepared and stirred for 30 minutes at this temperature. The pH is brought to 10.0 by addition of NaOH, and maintained at this value for 2 hours at this temperature. The aim of this pH treatment is to inhibit the natural pentosanase activity without modification of substrate properties. After 2 hours at pH 10.0 the pH is adjusted to 4.70 with acetic acid. The insoluble part is separated by centrifugation and/or filtration. The pH is corrected to 4.70 if necessary. This substrate is stored frozen in 100 ml portions in plastic bottles.

C2. Enzyme solutions

The enzymatic product is diluted with water until the solution contains between 6 and 15 xylanase units per ml. Solutions containing insoluble matter are filtered before use.

D. Measurement

Equilibrate the viscosimeter in the 42° C. water-bath for at least 30 minutes before measuring. Place a tube containing exactly 20 ml of substrate in the bath and wait until the temperature is constant. Add 2 ml of the enzyme solution at Zero time recorded on the stop-watch No. 1, mix and transfer the quantity needed to the viscosimeter. Measure the viscosity of the mixture after 3 minutes, then every 3 minutes for about 15 minutes.

Draw the mixture into the upper reservoir and allow the liquid to flow down; as soon as the meniscus of the liquid reaches the upper mark, start stop-watch No. 2 and read at the same time the time T recorded on the stop-watch No. 1.

As soon as the meniscus of the liquid reaches the lower mark, stop stop-watch No. 2 and record the time $\Delta t$ in seconds taken by the liquid to flow through the capillary tube. Reset stop-watch No. 2 and repeat the determination of t for the different times T, as indicated previously.

For each series of determinations determine the minimum viscosity corresponding to the end of the enzymatic reaction by allowing the substrate and an excess of enzyme to react on the substrate under the conditions of the test ($\Delta tm$). Moreover, determine $\Delta t0$ corresponding to the viscosity of 20 ml substrate and 2 ml water. Verify the stability of this value during all analyses.

The same analysis is carried out with the standard enzyme preparation.

E. Calculation

E1. Determination of the K constants

For each assay and for the standard: calculate the time t (seconds) of each measurement:

$$t = T + \frac{\Delta t}{2}$$

for each t calculate the ratio $$I/ns = \frac{\Delta to - \Delta tm}{\Delta t - \Delta tm}$$

Plot the successive values of t against the corresponding values of I/nS in a graph. Draw the curve which should be a straight line and determine the slope K (seconds$^{-1}$) of this line which is taken as the apparent kinetics constant.

E2. Calculation of the activity

For the xylanase standard we have:
reference activity As (xylanase units/g)
enzymatic concentrations of the solution assayed Cs (g/l)
apparent kinetics constant Ks
For the unknown xylanase to be measured we have:
enzymatic concentration of the solution assayed Ce (g/l)
apparent kinetics constant Ke The calculation of the unknown activity compared to the standard is:

$$\text{activity} = As \times \frac{Cs}{Ce} \times \frac{Ke}{Ks} = \text{xylanase units/g or ml.}$$

EXAMPLE I

Comparison of endo-xylanase activity of xylanases derived from *Disporotrichum dimorphosporum, Trichoderma* and *Aspergillus niger* by Drews method The endo-xylanase activity was determined by the method described by Drews and Weipert, Die Müllerei, 15, 369 (1970). The activity determined in this way appeared to agree very well with the technological effects of xylanase in brewing.

A dispersion of 150 g of grey rye flour (170 type) in 350 ml of tap water at 42° C. was prepared. The slurry was introduced in the bowl of a Brabender viscosigraph maintained at 42° C. After stabilization of the viscosity, 10 ml of an enzymatic solution containing 60 xylanase units measured by reducing sugars determination was introduced in the viscosigraph. After 10, 20 and 30 minutes of enzymatic hydrolysis the percentage of viscosity decrease was measured.

At 42° C., starch was not gelatinized and alpha-amylase had no effect. It was also verified that amylases, proteases and beta-glucanases had no significant effect.

It is possible to use the liquid fraction obtained after centrifugation of the rye flour dispersion as viscous substrate. The Brabender viscosigraph can then be replaced by an Ostwald type viscosimeter. These two methods give similar results (cf. the procedure described on page 9 ff.).

FIGS. 4, 5 and 6 show the effect of Aspergillus, Disporotrichum and Trichoderma xylanases at the same amount of activity units measured according to the reducing sugars determination method (usual method).

FIG. 4 shows that Aspergillus xylanase had no effect on the pentosanes viscosity which remains stable in function of time. This product contains only an exo-xylanase.

FIG. 5 shows the effect of Disporotrichum xylanase with a typical continuous viscosity decrease in function of time. This curve is typical for endo-xylanase activity.

FIG. 6 shows the effect of Trichoderma xylanase: a rapid viscosity decrease within the first 1-2 minutes, whereafter the viscosity remains stable during the rest of the time. This curve is characteristic for the inhibitory effect or steric hindrance concerning this enzyme.

*Talaromyces emersonii* xylanase shows the same typical curve as Disporotrichum xylanase, but the level of xylanase activity is dramatically lower in Talaromyces commercial products (between 50 and 150 endo-xylanase units per ml into Glaxo commercial beta-glucanase).

EXAMPLE II

Comparison of xylanase activity of xylanases derived from Disporotrichum and Trichoderma on different substrates and according to different methods

| ANALYTICAL METHODS | ACTIVITY RATIO of Trichoderma xylanase to Disporotrichum xylanase |
|---|---|
| Reductimetric acitivity on corn cob xylans | 21.8 |
| Viscosimetric method on Brabender viscosigraph (Drews) - total rye substrate, see Example I | about 6 |
| Viscosimetric method with Ostwald viscosimeter - soluble rye substrate, see procedure on p. 9 | about 9 |
| Viscosimetric method with Ostwald viscosimeter and purified rye substrate by alcohol precipitation | from 3.4 to 15 |
| Viscosimetric method with Ostwald viscosimeter on soluble rye substrate previously heated 20 min at 90° C. | 31.5 |

The first analysis was realized on corn cob xylans with monosaccharide determination by reductimetry. In this case both exo- and endo-xylanase activities were measured. It is difficult to estimate the activity of Trichoderma xylanases using the viscosimetric method on a Brabender or Ostwald viscosimeter because the results were highly dependent on the enzymatic concentration used. This indicates an inhibitory effect.

Use of ethanol precipitated rye xylans as a purified substrate for viscosimetric analysis did not modify the results. Moreover it was also verified that the action of several proteases did not modify either the soluble substrate nor the inhibitory effect for Trichoderma xylanase. However, heating the soluble substrate promoted the precipitation of an insoluble substance containing 65% of proteins and 35% of carbohydrates mainly xylose, arabinose and glucose. With this heated soluble substrate an improvement of the activity of Disporotrichum xylanase by a factor of 5 and an improvement of the activity of Trichoderma xylanase by a factor of 20 were obtained. Thus the inhibitory effect is more important on this latter xylanase.

EXAMPLE III

The influence of xylanases on wort at laboratory scale

Conditions

Use of poor quality malt, i.e. a malt giving low extract yield and low filterability in brewing industry due to high level of non-degraded beta-glucans and hemicelluloses.

Malt is ground with the EBC MIAG mill according to the standard specifications for lauter tun filtration.

Standard brewing process:

One part of malt is hydrated with 3 parts of water at 50° C. (note the start weight of each trial). This temperature is maintained during 20 minutes.

Heat at 63° C. per 1° C./minute. This temperature is maintained during 30 minutes.

Heat at 72° C. per 1° C./minute. This temperature is maintained during 20 minutes in order to obtain complete saccharification (yellow color with iodine test).

Heat at 76° C. This temperature is maintained during 5 minutes.

Control the weight of each trial and add some water to obtain the start weight (water evaporation). Pour the mash for filtration into a funnel containing Schleicher and Schuell paper filter (EBC). Measure the volume of filtered wort in function of time. Specific gravity is determined at the end of filtration. This value allows to calculate extract and yield.

Viscosity of wort is measured with a capillary viscosimeter at 20° C. High molecular weight beta-glucans is determined after precipitation with 30% ammonium sulfate. The precipitate is washed with alcohol before acid hydrolysis and determination of glucose with orcinol reagent.

The xylanase activity shown in the Tables hereinafter is measured by the viscosimetric method described on page 9 ff.

(a) Comparison between Disporotrichum and Trichoderma xylanases

The results are shown in Table I. These experiments clearly demonstrate the better efficiency of Disporotrichum xylanase in comparison with Trichoderma xylanase. See also the explanation in Examples I and II.

TABLE 1

| Analysis of wort | Disporotrichum xylanase | | Trichoderma xylanase | | |
|---|---|---|---|---|---|
| | 100 units/ kg malt | 300 units/ kg malt | 125 units/ kg malt | 250 units/ kg malt | 375 units/ kg malt |
| filtered volume (ml) after | | | | | |
| 2 min | 34 | 45 | 30 | 31 | 31 |
| 4 min | 54 | 69 | 45 | 48 | 47 |
| 6 min | 69 | 88 | 56 | 60 | 58 |
| 8 min | 80 | 103 | 66 | 69 | 68 |
| 10 min | 90 | 116 | 73 | 77 | 74 |
| specific gravity | 1.0798 | 1.0806 | 1.0798 | 1.0796 | 1.0796 |
| viscosity (mPa/s) | 2.57 | 2.51 | 2.82 | 2.78 | 2.75 |

(b) Comparison between different commercial products containing beta-glucanase with or without Disporotrichum xylanases added, increasing the filterability of wort Three commercial products containing beta-glucanase from different sources were compared with respect to the filterability of wort with one of them, to which Disporotrichum xylanase was added. The results are shown in Table 2.

These experiments confirm the better efficiency of Disporotrichum xylanase on wort viscosity, extract and filterability. The relative good results obtained with the geta-glucanase sample from Glaxo are due to some xylanase activity (165 u/g).

TABLE 2

| Analysis of wort | No enzyme control | 0.1% betaglucanase (Penicillium emersonii from Glaxo) | 0.1% betaglucanase Grindazym (Aspergillus niger from Grindstedt) | 0.1% betaglucanase Filtrase AM (Bacillus subtilis from Gist-Brocades) | 0.1% betaglucanase Filtrase AM + 600 u/g Disporotrichum xylanase |
|---|---|---|---|---|---|
| Filtered volume (ml) after | | | | | |
| 2 min | 18 | 25 | 22 | 22 | 39 |
| 4 min | 25 | 47 | 36 | 37 | 82 |
| 6 min | 29 | 58 | 47 | 50 | 107 |
| 8 min | 34 | 69 | 54 | 60 | 126 |
| 10 min | 39 | 77 | 62 | 69 | 146 |
| Extract g/100 g | 20.46 | 20.64 | 20.64 | 20.73 | 20.79 |
| Viscosity (mPa/s) | 3.58 | 2.88 | 3.33 | 3.20 | 2.73 |

(c) Comparison between different formulations: blend of *Bacillus subtilis* beta-glucanase+Disporotrichum xylanase, *Penicillium emersonii* beta-glucanase and *Penicillium emersonii* beta-glucanase with Disporotrichum xylanase added increasing the filterability of wort (1) The wort is 100% Menuet 81 malt from Stella Artois Brewery. The results are shown in Table 3.
(2) The wort is 100% malt from "Enfants de Gayant" Brewery. The results are shown in Table 4.

The combinations *Penicillium emersonii* beta-glucanase+Disporotrichum xylanase and *Bacillus subtilis* beta-glucanase+Disporotrichum xylanase gave about similar results.

(3) The wort is 60% Menuet 81 malt (from Stella Artois Brewery)+40% Menuet 82 barley. The results are shown in Table 5.

If the results in this Table 5 are compared with those in the Tables 3 and 4 it will be clear that the higher viscosity caused by the use of barley in the mash is most efficiently reduced by the use of Disporotrichum xylanase.

TABLE 3

| | No enzyme control | Blend of 300 u/g B. subtilis β-glucanase 0.05% + 400 u/g Disporotrichum xylanase 0.1% | | Penicillium emersonii β-glucanase (Glaxo) 0.1% | P. emersonii β-glucanase + 150 u/g Disporotrichum xylanase 0.1% |
|---|---|---|---|---|---|
| Filtered volume (ml) after | | | | | |
| 2 min | 22 | 60 | 60 | 62 | 62 |
| 4 min | 50 | 84 | 84 | 94 | 92 |
| 6 min | 63 | 112 | 114 | 102 | 118 |
| 8 min | 75 | 134 | 140 | 138 | 142 |
| 10 min | 82 | 152 | 154 | 156 | 162 |
| Specific gravity (20° C./20° C.) | 1.0827 | 1.0832 | 1.0838 | 1.0831 | 1.0838 |
| Extract (g/100 g) | 19.95 | 20.05 | 20.18 | 20.03 | 20.18 |
| Yield/d.s. (%) | 82.66 | 83.18 | 83.84 | 83.07 | 83.84 |
| Viscosity (mPa/s) | 3.14 | 2.66 | 2.64 | 2.77 | 2.63 |
| β-glucans (mg/l) | 1 105 | 260 | 212 | 660 | 280 |

TABLE 4

| | No enzyme control | Blend of 300 u/g B. subtilis β-glucanase 0.05% + 400 u/g Disporotrichum xylanase 0.1% | | Penicillium emersonii β-glucanase (Glaxo) 0.1% | P. emersonii β-glucanase + 150 u/g Disporotrichum xylanase 0.1% |
|---|---|---|---|---|---|
| Filtered volume (ml) after | | | | | |
| 2 min | 32 | 68 | 80 | 54 | 78 |
| 4 min | 50 | 100 | 118 | 78 | 118 |
| 6 min | 63 | 132 | 152 | 104 | 158 |
| 8 min | 74 | 154 | 178 | 122 | 182 |
| 10 min | 83 | 172 | 196 | 138 | 196 |
| Specific gravity (20° C./20° C.) | 1.0825 | 1.0834 | 1.0842 | 1.0828 | 1.0840 |
| Extract (g/100 g) | 19.89 | 20.10 | 20.27 | 19.96 | 20.23 |
| Yield/sec. (%) | 80.46 | 81.52 | 82.38 | 80.81 | 82.18 |
| Viscosity (mPa/s) | 3.20 | 2.69 | 2.67 | 2.73 | 2.66 |
| β-glucans (mg/l) | 2 500 | 340 | 295 | 1 540 | 940 |

TABLE 5

| | No enzyme control | Blend of 300 u/g B. subtilis β-glucanase 0.05% + 400 u/g Disporotrichum xylanase 0.1% | | Penicillium emersonii β-glucanase (Glaxo) 0.1% | P. emersonii β-glucanase + 150 u/g Disporotrichum xylanase 0.1% |
|---|---|---|---|---|---|
| Filtered volume (ml) after | | | | | |
| 2 min | 31 | 78 | 92 | 80 | 90 |
| 4 min | 48 | 118 | 146 | 120 | 140 |
| 6 min | 57 | 150 | 180 | 150 | 172 |
| 8 min | 66 | 176 | 200 | 168 | 198 |
| 10 min | 70 | 196 | 214 | 176 | 208 |
| Specific gravity (20° C./20° C.) | 1.0760 | 1.0797 | 1.0806 | 1.0780 | 1.0805 |
| Extract (g/100 g) | 18.42 | 19.26 | 19.47 | 18.98 | 19.44 |
| Yield/sec. (%) | 78.06 | 81.36 | 82.46 | 89.89 | 82.30 |
| Viscosity (mPa/s) | 3.37 | 2.67 | 2.55 | 2.69 | 2.58 |
| β-glucans (mg/l) | 3 910 | 840 | 659 | 2 800 | 1 890 |

EXAMPLE IV

Colloidal stability of beer improved by Disporotrichum xylanase

The colloidal stability of filtered untreated beer on laboratory scale was determined under the same conditions using the alcohol cooling test according to M. Moll, V. That, A. Schmitt and M. Parisot, J. Amer. Soc. Brew. Chem., 34, 187 (1976): a certain amount of enzyme, specified in Table 6, was introduced in short volume into the bottles. The enzymatic solution was solified in order to avoid dilution by the introduction of beer. The bottles were closed immediately after introduction of beer in order to avoid oxidation. The bottles were stored for one week at room temperature and the efficiency of the enzymatic treatment with the alcohol cooling test was measured. The lower the EBC haze value, the more efficient the enzymatic product. The results are shown in the following Table 6.

TABLE 6

| Papain concentration (NF units/ Hl) | Haze value (Hazemeter) E.B.C. units | | | |
|---|---|---|---|---|
| | papain alone | papain + 1500 u/Hl B. subtilis -glucanase | papain + 1200 u/Hl Disporotrichum xylanase | papain + 3000 u/Hl Disporotrichum xylanase |
| 6100 | 10.5 | 10.4 | 9.8 | 7.8 |
| 9200 | 3.6 | 3.7 | 3.9 | 2.3 |
| 12200 | 2.1 | 3.1 | 0.6 | 0.8 |

TABLE 6-continued

| Papain concentration (NF units/Hl) | Haze value (Hazemeter) E.B.C. units | | | |
|---|---|---|---|---|
| | papain alone | papain + 1500 u/Hl B. subtilis -glucanase | papain + 1200 u/Hl Disporotrichum xylanase | papain + 3000 u/Hl Disporotrichum xylanase |
| 18400 | 1.9 | 2.5 | 0.4 | 0.6 |

The minimum haze value obtained with an excess dose of papain was further decreased when Disporotrichum xylanase was used in addition to papain.

What I claim is:

1. A process for improving the filterability of wort or beer comprising treating said wort or beer with xylanase produced by *Disporotrichum dimorphosporum* in an amount effective to improve the filterability.

2. The process of claim 1 wherein the said xylanase is derived from *Disporotrichum dimorphosporum* ATCC 24562.

3. The process of claim wherein papain is also added to the wort or beer in an amount sufficient to improve filterability of the beer.

4. The process of claim 1, wherein unmalted wheat or barley is used to make the wort or beer.

* * * * *